(12) United States Patent
Cezo

(10) Patent No.: US 12,727,773 B2
(45) Date of Patent: Sep. 8, 2026

(54) RENAL VASCULAR RESISTANCE USING INTRAVASCULAR BLOOD FLOW AND PRESSURE AND ASSOCIATED SYSTEMS, DEVICES, AND METHODS

(71) Applicant: KONINKLIJKE PHILIPS N.V., Eindhoven (NL)

(72) Inventor: James David Cezo, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 690 days.

(21) Appl. No.: 18/099,152

(22) Filed: Jan. 19, 2023

(65) Prior Publication Data

US 2023/0233095 A1 Jul. 27, 2023

Related U.S. Application Data

(60) Provisional application No. 63/302,440, filed on Jan. 24, 2022.

(51) Int. Cl.
*A61B 5/026* (2006.01)
*A61B 5/00* (2006.01)
(Continued)

(52) U.S. Cl.
CPC .......... *A61B 5/026* (2013.01); *A61B 5/02158* (2013.01); *A61B 5/6852* (2013.01);
(Continued)

(58) Field of Classification Search
CPC ... A61B 5/026; A61B 5/02158; A61B 5/6852; A61B 5/742; A61B 2562/0247;
(Continued)

(56) References Cited

U.S. PATENT DOCUMENTS 10,743,774 B2 * 8/2020 Suh ...................... A61B 5/0215
10,980,426 B2 * 4/2021 Manstrom ........... A61B 5/6851
(Continued)

FOREIGN PATENT DOCUMENTS

EP 3686898 A1 7/2020

OTHER PUBLICATIONS

U.S. Appl. No. 63/300,536, filed Jan. 18, 2022.

*Primary Examiner* — Jeffrey G. Hoekstra

(57) ABSTRACT

A system includes a processor circuit configured to receive a first set of data. The first set of data includes two pressure measurements and a flow measurement from the vasculature of a patient obtained while the sympathetic nervous system of the patient is not under stimulation. The processor circuit calculates a blood flow resistance value based on the first set of data. The processor circuit then receives a second set of data. The second set of data also includes two pressure measurements and a flow measurement from the vasculature of the patient obtained while the sympathetic nervous system of the patient is stimulated. The processor circuit calculates another blood resistance value based on the second set of data. The processor circuit then compares the two blood flow resistance values to determine whether a denervation procedure would be effective to mitigate the nerve system's response to stimulation. The processor circuit outputs to a screen display metrics obtained from the measurement procedure.

17 Claims, 10 Drawing Sheets

(51) Int. Cl.
*A61B 5/0215* (2006.01)
*G16H 40/63* (2018.01)
*G16H 50/50* (2018.01)

(52) U.S. Cl.
CPC ............. *A61B 5/742* (2013.01); *G16H 40/63* (2018.01); *G16H 50/50* (2018.01); *A61B 2562/0247* (2013.01); *A61B 2562/04* (2013.01)

(58) Field of Classification Search
CPC . A61B 2562/04; A61B 5/4041; A61B 5/0215; A61B 18/1492; A61B 2018/00404; A61B 2018/00511; A61B 2018/00577; A61B 5/02007; G16H 40/63; G16H 50/50; A61N 1/36007; A61N 1/36117
See application file for complete search history.

(56) References Cited

U.S. PATENT DOCUMENTS

| | | | | |
|---|---|---|---|---|
| 11,160,513 | B2 * | 11/2021 | Anderson | A61B 5/743 |
| 11,826,128 | B2 * | 11/2023 | Hiltner | A61M 25/09 |
| 12,315,076 | B1 * | 5/2025 | Farkash | G06T 3/10 |
| 12,354,755 | B2 * | 7/2025 | Benishti | A61B 5/026 |
| 12,387,325 | B2 * | 8/2025 | Shalhon Livne | G06T 7/0016 |
| 12,408,885 | B2 * | 9/2025 | Lavi | G06T 7/149 |
| 2013/0190633 | A1 * | 7/2013 | Dorando | A61B 5/7475 600/486 |
| 2014/0180087 | A1 * | 6/2014 | Millett | A61B 5/02158 600/437 |
| 2015/0133799 | A1 * | 5/2015 | O'Connell | A61B 5/0215 600/486 |
| 2015/0196210 | A1 * | 7/2015 | McCaffrey | A61M 25/007 600/488 |
| 2016/0183808 | A1 | 6/2016 | Kohler | |
| 2018/0280088 | A1 | 10/2018 | Davies | |
| 2021/0236001 | A1 | 8/2021 | Van Der Horst | |

* cited by examiner 400
402
492 494
416
414
480
410
490
412
482
491

400
502
492 494
514
516
510
580
482
590
512
491

400
602
492 494
614
616
Pressure Sensor
612
610
482
491

RENAL VASCULAR RESISTANCE USING INTRAVASCULAR BLOOD FLOW AND PRESSURE AND ASSOCIATED SYSTEMS, DEVICES, AND METHODS

CROSS-REFERENCE TO RELATED APPLICATIONS

This application claims priority to and the benefit of U.S. Provisional Application No. 63/302,440, filed Jan. 24, 2022, which is incorporated by reference herein in their entirety.

TECHNICAL FIELD

The present disclosure relates generally to renal vascular resistance within the renal artery based on blood pressure and blood flow measurements. The renal vascular resistance can indicate whether or not a patient is a good candidate for renal denervation or whether or not a given location of the blood vessel is a good location for renal denervation.

BACKGROUND

Physicians use many different medical diagnostic systems and tools to monitor a patient's health and diagnose medical conditions. In the field of assessing and treating hypertension in patients, various systems and devices are used to monitor a patient's condition and perform treatment procedures. One treatment procedure used to address hypertension of a patient is renal denervation. Renal denervation involves ablating or otherwise disabling the nerves of the renal artery. Because the renal nerves cause the renal artery to expand or contract in response to various stimuli, the renal nerves may be a cause of unnecessary high blood pressure in a patient. By disabling these nerves, blood pressure may be decreased.

However, renal denervation is not an effective treatment in all patients or at all locations within the renal vasculature of a patient. It is often difficult for a physician to determine whether a renal denervation will effectively address hypertension for a patient as results of renal denervation are highly patient-specific. As a result, a physician may perform a renal denervation procedure without success. This may be because the patient was not a patient which would respond positively to a renal denervation procedure or because the renal denervation procedure was performed in an incorrect region of the renal vasculature. Performing a renal denervation procedure with little to no effect on the patient unnecessarily subjects a patient to a traumatic and time-consuming procedure and wastes costly resources.

SUMMARY

Embodiments of the present disclosure are systems, devices, and methods for measuring renal vascular resistance using intravascular blood flow and pressure measurements. Aspects of the present disclosure advantageously provide a physician with a way to more accurately predict whether a patient will respond positively to a renal denervation procedure, which locations within the patient's renal vasculature are most suitable for a renal denervation procedure, whether a denervation procedure was successful in reducing hypertension of a patient, and to what extent the denervation procedure was successful. Aspects of the disclosure may provide a physician with more accurate measurements of the response of a patient to stimulation of the sympathetic nervous system.

The system disclosed includes an intravascular device which simultaneously acquires blood pressure data from two locations within the renal artery and blood flow data from at least one location within the same artery. The system automatically determines measurements of blood flow resistance based on these data. Blood flow resistance may be measured while sympathetic nervous system is stimulated and while the sympathetic nervous system is not stimulated. The resistance under stimulation is compared to the baseline resistance, or the resistance while the sympathetic nervous system is not stimulated. A change in these resistance measurements indicates that the patient is a good candidate for renal denervation or that the position within the renal artery of the device is a good position for the renal denervation device. These measurements may be displayed to the user via the screen display as numerical values, or any suitable type of visual or graphical representation. Little to no change in these resistance measurements may indicate that the patient is not a good candidate for renal denervation or that the location is not a good location for renal denervation.

In an exemplary aspect, a system is provided. The system includes a processor circuit configured to: receive, from a plurality of sensors, a first set of data associated with blood within a blood vessel of a patient, wherein the plurality of sensors comprises a first pressure sensor, a second pressure sensor, and a flow sensor, wherein the first set of data is obtained without stimulation of a sympathetic nervous system of the patient; determine a first blood flow resistance based on the first set of data; generate a visual representation of the first blood flow resistance; receive, from the plurality of sensors, a second set of data associated with the blood within the blood vessel, wherein the second set of data is obtained with stimulation of the sympathetic nervous system; determine a second blood flow resistance based on the second set of data; generate a visual representation of the second blood flow resistance; and output a screen display to a display in communication with the processor circuit, wherein the screen display comprises the visual representation of the first blood flow resistance and the visual representation of the second blood flow resistance.

In one aspect, the blood vessel comprises a renal artery, and wherein the nerve comprises a renal nerve. In one aspect, the first set of the data and the second set of data are obtained while: the first pressure sensor and the flow sensor are positioned within the blood vessel; and the second pressure sensor is positioned outside of a body of the patient, wherein the second pressure sensor is in direct fluid communication with the blood within the blood vessel. In one aspect, the first set of the data and the second set of data are obtained while the first pressure sensor, the second pressure sensor, and the flow sensor are positioned within the blood vessel. In one aspect, the system includes a first intravascular catheter or guidewire comprising the first pressure sensor and the flow sensor. In one aspect, the system includes a second intravascular catheter or guidewire comprising the second pressure sensor. In one aspect, the system includes an intravascular catheter or guidewire, wherein the intravascular catheter or guidewire comprises the first pressure sensor, the second pressure sensor, and the flow sensor. In one aspect, the first set of data and the second set of data each respectively comprise: a first pressure measurement obtained by the first pressure sensor; a second pressure measurement obtained by the second pressure sensor; and a flow measurement obtained by the flow sensor. In one aspect, the first pressure measurement, the second pressure measurement, and the flow measurement are obtained simultaneously. In one aspect, the processor circuit is configured to perform a comparison based on the first blood flow resistance and the second blood flow resistance, wherein the comparison comprises a determination of whether a difference between the first blood flow resistance and the second blood flow resistance exceeds a threshold difference, wherein the screen display comprises a visual representation based on the determination. In one aspect, the processor circuit is configured to perform a comparison based on the first blood flow resistance and the second blood flow resistance, wherein the comparison comprises a determination of whether denervation is recommended for the patient, and wherein the screen display comprises a visual representation based on the determination. In one aspect, the processor circuit is configured to: perform a comparison based on the first blood flow resistance and the second blood flow resistance; and determine a location for a renal denervation procedure based on the comparison, wherein the screen display comprises a visual representation based on the location. In one aspect, the processor circuit is configured to: perform a comparison based on the first blood flow resistance and the second blood flow resistance; and determine if a renal denervation procedure was successful based on the comparison, and wherein the screen display comprises a visual representation based on the determination of if the renal denervation procedure was successful. In one aspect, the first set of data and the second set of data are obtained during a first measurement procedure, wherein, during a second measurement procedure, the processor circuit is further configured to: determine a third blood flow resistance based on a third set of data and a fourth blood flow resistance based on a fourth set of data; and output a further screen display to the display, wherein the further screen display comprises a visual representation of the third blood flow resistance and the fourth blood flow resistance.

In an exemplary aspect, a method is provided. The method includes receiving, with a processor circuit, a first set of data associated with blood within a blood vessel of a patient from a plurality of sensors, wherein the plurality of sensors comprises a first pressure sensor, a second pressure sensor, and a flow sensor, wherein the first set of data is obtained without stimulation of a sympathetic nervous system of the patient; determining, with the processor circuit, a first blood flow resistance based on the first set of data; generating, with the processor circuit, a visual representation of the first blood flow resistance; receiving, with the processor circuit, a second set of data associated with the blood within the blood vessel from the plurality of sensors, wherein the second set of data is obtained with stimulation of the sympathetic nervous system; determining, with the processor circuit, a second blood flow resistance based on the second set of data; generating, with the processor circuit, a visual representation of the second blood flow resistance outputting, with the processor circuit, a screen display to a display in communication with the processor circuit, wherein the screen display comprises the visual representation of the first blood flow resistance and the visual representation of the second blood flow resistance.

In an exemplary aspect, a system is provided. The system includes an intravascular catheter or guidewire configured to be positioned within a renal artery of a patient, wherein the intravascular catheter or guidewire comprises a first pressure sensor and a flow sensor; a second pressure sensor; and a processor circuit configured for communication with the first pressure sensor, the second pressure sensor, and the flow sensor, wherein the processor circuit is configured to: receive a first set of data associated with blood within the renal artery and obtained without stimulation of a sympathetic nervous system of the patient; determine a first renal vascular resistance based on the first set of data; generate a visual representation of the first renal vascular resistance; receive a second set of data associated with the blood within the renal artery, wherein the second set of data is obtained with stimulation of the sympathetic nervous system; determine a second renal vascular resistance based on the second set of data; generate a visual representation of the second renal vascular resistance; and output a screen display to a display in communication with the processor circuit, wherein the screen display comprises the visual representation of the first renal vascular resistance and the visual representation of the second renal vascular resistance, wherein the first set of data and the second set of data each respectively comprise: a first pressure measurement obtained by the first pressure sensor; a second pressure measurement obtained by the second pressure sensor; and a flow measurement obtained by the flow sensor.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
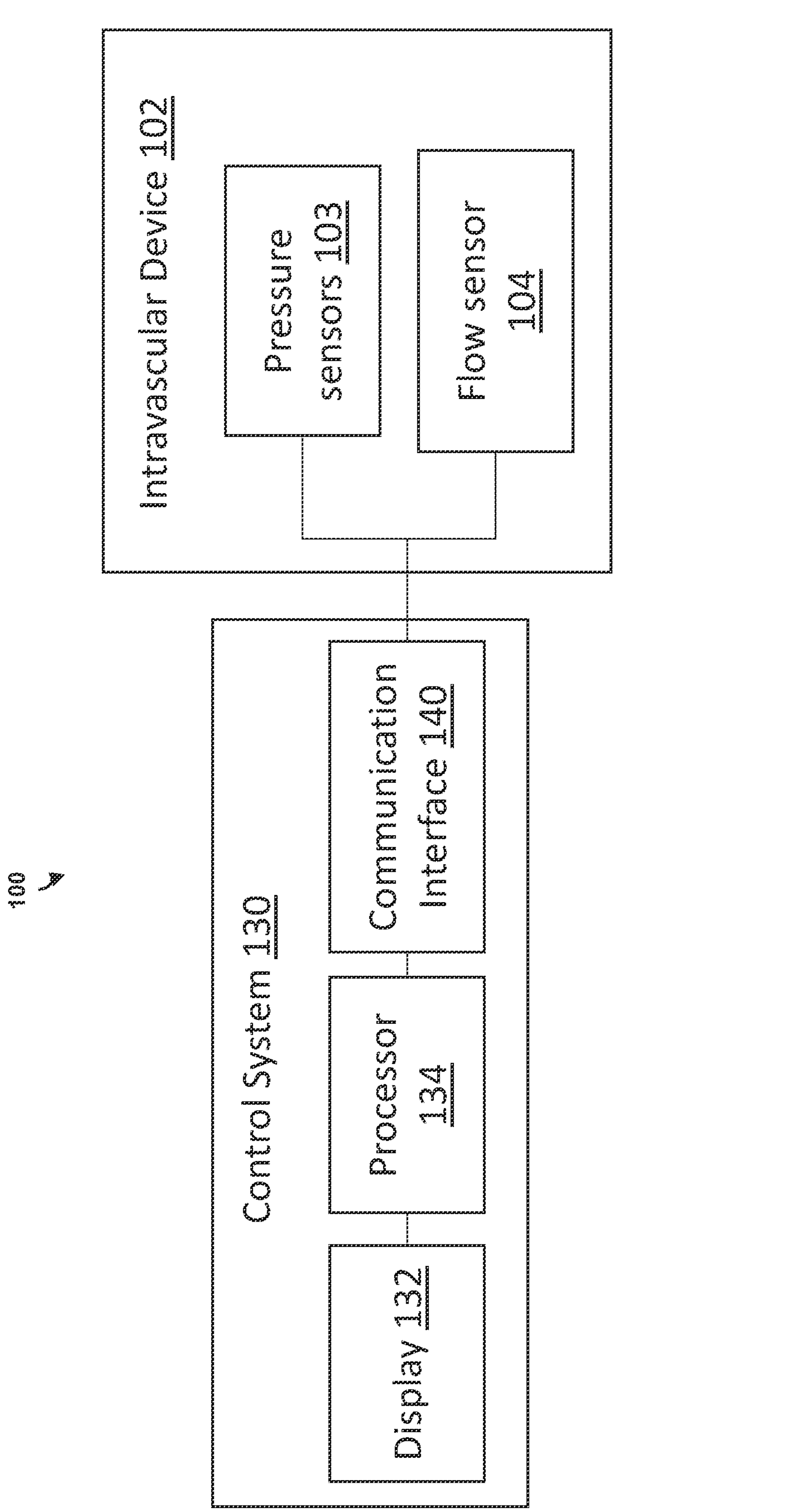
FIG. 1 is a diagrammatic schematic view of a physiological measurement system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Aspects of the present disclosure may include various principles described in U.S. patent application Ser. No. 18/086,511, filed Dec. 21, 2022.

FIG. 1 is a diagrammatic schematic view of a physiological measurement system 100, according to aspects of the present disclosure. The system 100 may include a processor 134, a display 132, and a communication interface 140, as well as any other suitable components. The system 100 may be a system comprising a processor circuit configured for communication with an intravascular device 102. The intravascular device 102 may include any suitable type of measurement sensors or devices. For example, the intravascular device 102 may be or include a catheter, a guidewire, or any other suitable devices. The processor circuit may be the processor circuit 210 described with reference to FIG. 2. The display 132 may also be referred to as a monitor. The system 100 can be a pressure and flow measurement system. The system 100 may include an intraluminal device 102 such as a catheter, guide wire, or guide catheter, a communication interface module 140, and a display 132.

The device 102 can be sized, shaped, or otherwise configured to be positioned within the body lumen of a patient. The communication interface 140 may be configured to transfer the received data to the processor 134 (also referred to as a computer or console) where the data is processed, reconstructed, and/or displayed on the display 132. The console or computer 134 can include a processor and a memory. The computer or computing device 134 can be operable to facilitate the features of the system 100 described herein. For example, the processor can execute computer readable instructions stored on a non-transitory tangible computer readable medium.

The communication interface 140 facilitates communication of signals between the processor 134 and various data measurement sensors or devices of the device 102. This communication may include the steps of: (1) providing commands to integrated circuit controller chip(s) to receive measurement data, (2) providing transmit trigger signals to components of the device 102, and/or (3) accepting signals or measurements received from the device 102.

FIG. 1 includes a control system 130. The control system 130 includes a display 132, a processor 134, and a communication interface 140. The control system 130 may be configured to communicate with an intravascular device 102. The intravascular device 102 may include one or more pressure sensors 103, and a flow sensor 104. It is anticipated that the intravascular device 102 may include additional sensors and or devices. In some embodiments, the intravascular device 102 may be configured, and/or sized and shaped, to be positioned within a renal artery of a patient. The pressure sensors 103 may receive pressure data corresponding to the blood within the renal artery of the patient. The flow sensor 104 may receive flow data, including blood flow data or blood velocity data. The communication interface 140 may be configured to receive any of the data collected by the pressure sensors 103 and or the flow sensor 104. The communication interface 140 may transmit this data to the processor 134 of the control system 130. The flow sensor 104 may be a vascular flow reserve sensor configured to measure vascular flow reserve, or a renal flow reserve sensor configured to measure renal flow reserve. The blood flow measurements shown in FIG. 5 may relate to blood velocity within a renal artery of a patient.

The intravascular device 102 may be configured to obtain various physiology data of a patient. For example, the device 102 may obtain medical data about a patient's body while the device 102 is positioned inside the patient's body. In some embodiments, the intravascular device 102 may be configured to receive pressure measurements by the pressure sensor 103 and flow measurements by the flow sensor 104.

In some embodiments, the system 100 may include additional components, such as a patient interface module (PIM) configured to facilitate communication between the intravascular device 102 and the control system 130. In some embodiments, a PIM may facilitate communication between one or more pressure sensors, such as the pressure sensors 103, and/or one or more flow sensors 104, with the control system 130. The system 100 may additionally include a transmission line bundle extending from the intravascular device 102 to the control system 130 (e.g., a PIM or the communication interface 140 of the control system 130). In some embodiments, the communication interface 140 may be a PIM.

In some embodiments, the intravascular device 102 obtains intraluminal (e.g., intravascular) pressure data. In some embodiments, the intraluminal system 100 is an intravascular pressure sensing system that determines pressure ratios based on the pressure data, such as fractional flow reserve (FFR), instantaneous wave-free ratio (iFR), and/or other suitable ratios between distal pressure and proximal/aortic pressure (Pd/Pa). In some embodiments, the intraluminal device 102 may obtain intraluminal (e.g., intravascular) flow data, and the intraluminal system 100 is an intravascular flow sensing system that determines flow-related values based on the pressure data, such as coronary flow reserve (CFR), flow velocity, flow volume, etc.

Aspects of the intravascular device 102 and the control system 130 will be described in more detail hereafter. For example, the intravascular device 102 may include multiple embodiments as described hereafter. In some embodiments, the system 100 may be a catheter-based system configured to measure fluid resistance of blood flow from the renal artery of a patient into the kidney of the patient. This measurement can be used to identify patients or assess success for renal denervation therapies, as will be described in more detail hereafter. In some embodiments, the use of flow and pressure sensors on a catheter body may allow the calculation of blood flow resistance in the kidney vasculature. In some aspects, an intravascular device or intravascular data may also be referred to as an endovascular device or endovascular data respectively. In some embodiments, the device may be referred to as an intraluminal, intra-cavity, or intra-body device. For example, the device may be positioned within a blood vessel or in any other body lumen/cavity, including outside a vessel and within the body, such as proximate to muscle or fat, around a renal vessel/nerve and kidney).

In some aspects, any of the systems, devices, sensors, methods, principles, and/or any teachings of the present disclosure may be similar to the teachings of U.S. Provisional Application No. 63/300,536, filed Jan. 18, 2022, and/or U.S. application Ser. No. 18/086,511, filed Dec. 21, 2022, each of which are incorporated by reference herein in its entirety.

Figure 2:
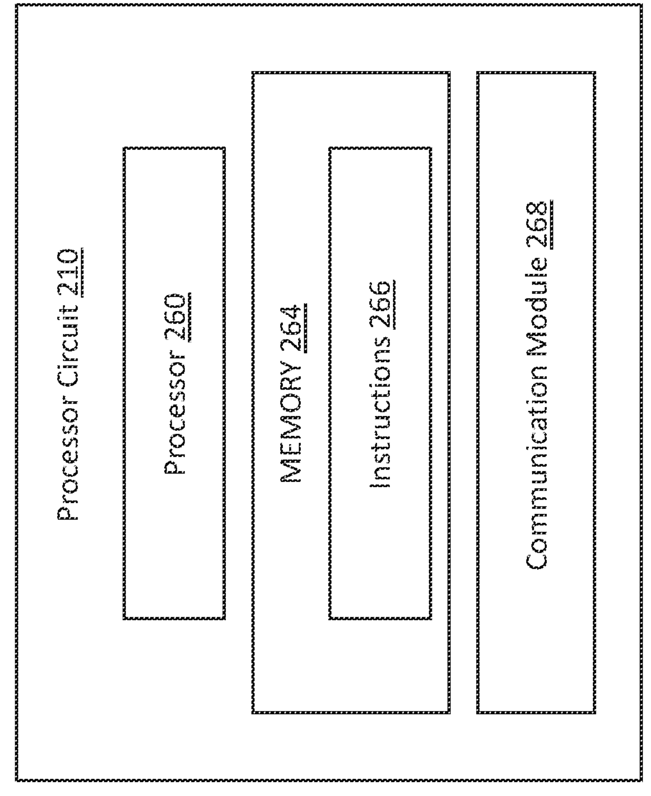
FIG. 2 is a schematic diagram of a processor circuit, according to aspects of the present disclosure.

FIG. 2 is a schematic diagram of a processor circuit, according to aspects of the present disclosure. The processor circuit 210 may be implemented in the control system 130 (e.g., as shown in FIG. 1), or any other suitable location. In an example, the processor circuit 210 may be in communication with any of the devices, systems, or subsystems described in the present disclosure. For example, the processor circuit 210 may be in communication with a blood flow sensing device, a pressure sensing device, an extraluminal imaging device, a nerve stimulation device, a nerve ablation device or any other device, system, or subsystem. The processor circuit 210 may include the processor 134 (FIG. 1) and/or a communication interface. One or more processor circuits 210 are configured to execute the operations described herein. As shown, the processor circuit 210 may include a processor 260, a memory 264, and a communication module 268. These elements may be in direct or indirect communication with each other, for example via one or more buses.

The processor 260 may include a CPU, a GPU, a DSP, an application-specific integrated circuit (ASIC), a controller, an FPGA, another hardware device, a firmware device, or any combination thereof configured to perform the operations described herein. The processor 260 may also be implemented as a combination of computing devices, e.g., a combination of a DSP and a microprocessor, a plurality of microprocessors, one or more microprocessors in conjunction with a DSP core, or any other such configuration.

The memory 264 may include a cache memory (e.g., a cache memory of the processor 260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 264 includes a non-transitory computer-readable medium. The memory 264 may store instructions 266. The instructions 266 may include instructions that, when executed by the processor 260, cause the processor 260 to perform the operations described herein with reference to any of the devices, system, or subsystems described. Instructions 266 may also be referred to as code. The terms “instructions” and “code” should be interpreted broadly to include any type of computer-readable statement(s). For example, the terms “instructions” and “code” may refer to one or more programs, routines, sub-routines, functions, procedures, etc. “Instructions” and “code” may include a single computer-readable statement or many computer-readable statements.

The communication module 268 can include any electronic circuitry and/or logic circuitry to facilitate direct or indirect communication of data between the processor circuit 210, the devices, systems, or subsystems described herein, the display 132, processor circuit 134, or communication interface 140 (FIG. 1). In that regard, the communication module 268 can be an input/output (I/O) device. In some instances, the communication module 268 facilitates direct or indirect communication between various elements of the processor circuit 210 and/or various described endovascular or extraluminal devices, systems, and/or the system 130 (FIG. 1).

Figure 3:
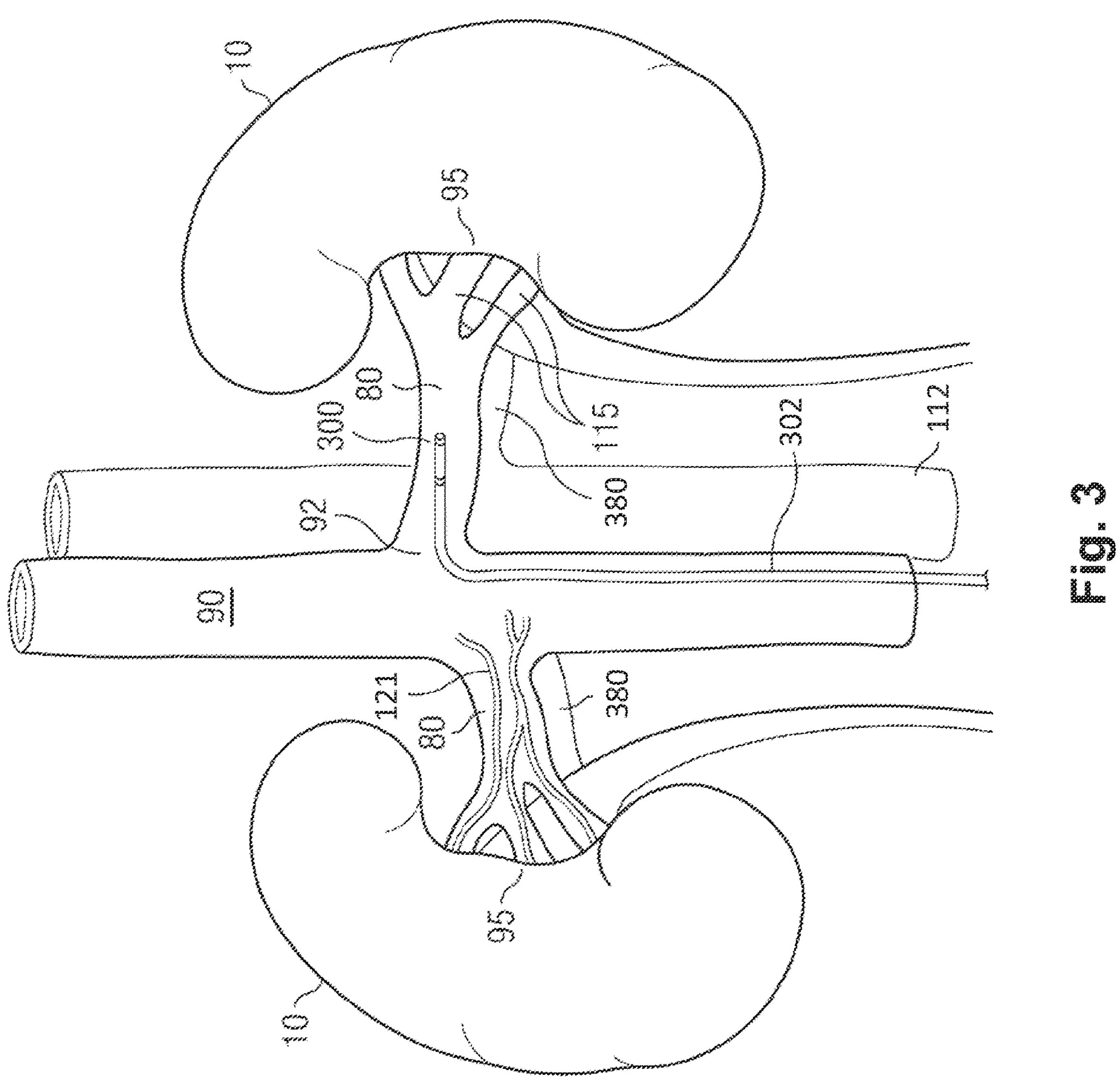
FIG. 3 is a diagrammatic view of an intravascular device positioned within the renal anatomy, according to aspects of the present disclosure.

FIG. 3 is a diagrammatic view of an intravascular device positioned within the renal anatomy, according to aspects of the present disclosure. FIG. 3 illustrates an intravascular device 302 disposed within the human renal anatomy. The human renal anatomy includes kidneys 10 that are supplied with oxygenated blood by right and left renal arteries 80, which branch off an abdominal aorta 90 at the renal ostia 92 to enter the hilum 95 of the kidney 10. The abdominal aorta 90 connects the renal arteries 80 to the heart (not shown). Deoxygenated blood flows from the kidneys 10 to the heart via renal veins 380 and an inferior vena cava 112. Specifically, a flexible elongate member of the intravascular device 302 is shown extending through the abdominal aorta and into the left renal artery 80. In alternate embodiments, the intravascular device 302 may be sized and configured to travel through the inferior renal vessels 115 as well. Specifically, the intravascular device 302 is shown extending through the abdominal aorta and into the left renal artery 80. In alternate embodiments, the catheter may be sized and configured to travel through the inferior renal vessels 115 as well.

Left and right renal plexi or nerves 121 surround the left and right renal arteries 80, respectively. Anatomically, the renal nerve 121 forms one or more plexi within the adventitial tissue surrounding the renal artery 80. For the purpose of this disclosure, the renal nerve is defined as any individual nerve or plexus of nerves and ganglia that conducts a nerve signal to and/or from the kidney 10 and is anatomically located on the surface of the renal artery 80, parts of the abdominal aorta 90 where the renal artery 80 branches off the aorta 90, and/or on inferior branches of the renal artery 80. Nerve fibers contributing to the plexi arise from the celiac ganglion, the lowest splanchnic nerve, the corticorenal ganglion, and the aortic plexus. The renal nerves 121 extend in intimate association with the respective renal arteries into the substance of the respective kidneys 10. The nerves are distributed with branches of the renal artery to vessels of the kidney 10, the glomeruli, and the tubules. Each renal nerve 121 generally enters each respective kidney 10 in the area of the hilum 95 of the kidney, but may enter the kidney 10 in any location, including the location where the renal artery 80, or a branch of the renal artery 80, enters the kidney 10.

Proper renal function is essential to maintenance of cardiovascular homeostasis so as to avoid hypertensive conditions. Excretion of sodium is key to maintaining appropriate extracellular fluid volume and blood volume, and ultimately controlling the effects of these volumes on arterial pressure. Under steady-state conditions, arterial pressure rises to that pressure level which results in a balance between urinary output and water and sodium intake. If abnormal kidney function causes excessive renal sodium and water retention, as occurs with sympathetic overstimulation of the kidneys through the renal nerves 121, arterial pressure will increase to a level to maintain sodium output equal to intake. In hypertensive patients, the balance between sodium intake and output is achieved at the expense of an elevated arterial pressure in part as a result of the sympathetic stimulation of the kidneys through the renal nerves 121. Renal denervation may help alleviate the symptoms and sequelae of hypertension by blocking or suppressing the efferent and afferent sympathetic activity of the kidneys 10.

In some embodiments, the vessel 80 is a renal vessel and various physiological parameters may be determined in the renal artery. Physiological parameters measured in the renal artery 80 may include blood pressure, blood flow, blood flow velocity, pulse wave velocity (PWV), strain or constriction of the vessel, voltage measurements of renal nerves, or any other parameters in the renal artery. The processing system 130 may determine a renal denervation therapy recommendation based on these parameters in a renal artery. For example, patients that are more likely or less likely to benefit therapeutically from renal denervation may be selected based on the parameters measured. In that regard, based on these parameters measured corresponding to the renal vessel, the processing system 230 can perform patient stratification for renal denervation.

Figure 4:
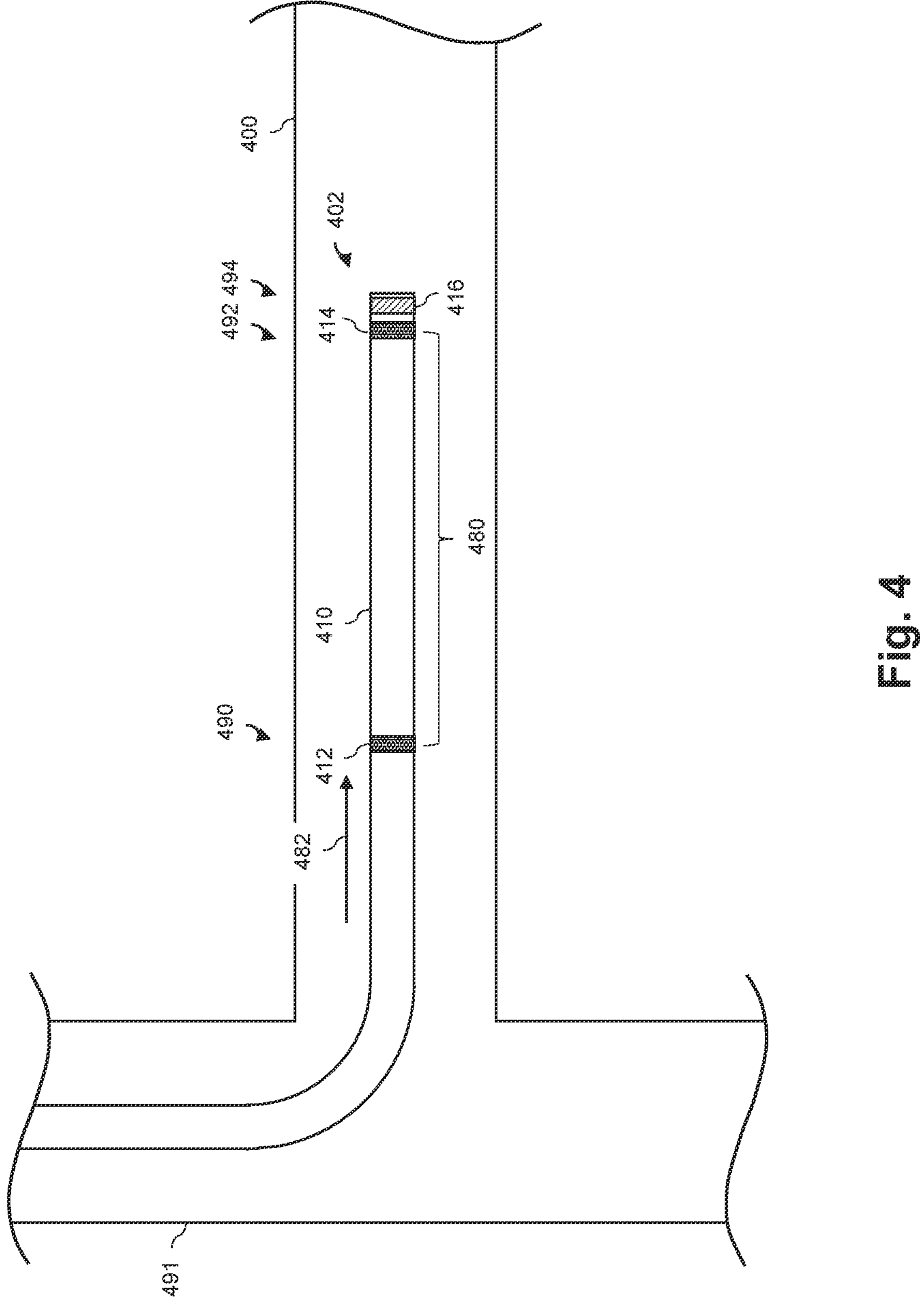
FIG. 4 is a diagrammatic view of an intravascular device positioned within the renal anatomy, according to aspects of the present disclosure.

FIG. 4 is a diagrammatic view of an intravascular device positioned within the renal anatomy, according to aspects of the present disclosure. The device 402 may be one embodiment of the device 102 described with reference to FIG. 1. As shown in FIG. 4, the device 402 may be configured to be positioned within a blood vessel 400 of a patient. For example, as shown in FIG. 4, a diagrammatic view of a blood vessel 400 is provided. The blood vessel 400 may be a renal artery of the patient. An aorta 491 is also shown. In some embodiments, the vessel 400 may be any suitable blood vessel or body lumen of a patient. The depiction of the vessel 400 with the vessel 491 shown in FIG. 4 is not intended to be limiting, but merely provides one example of one location within the patient vasculature where the intravascular device 402 may be positioned.

The device 402 may include a flexible elongate member 410, a proximal pressure sensor 412, a distal pressure sensor 414, and a blood flow sensor 416.

The flexible elongate member 410 may be sized and shaped, structurally arranged, and/or otherwise configured to be positioned within the body lumen 400 of a patient. The flexible elongate member 410 may be a part of guidewire and/or a catheter (e.g., an inner member and/or an outer member). The flexible elongate member 410 may be constructed of any suitable flexible material. For example, the flexible elongate member 410 may be constructed of a polymer material including polyethylene, polypropylene, polystyrene, or other suitable materials that offer flexibility, resistance to corrosion, and lack of conductivity. In some embodiments, the flexible elongate member 410 may define a lumen for other components to pass through. The flexible elongate member 410 may be sufficiently flexible to successfully maneuver various turns or geometries within the vasculature of a patient. The flexible elongate member 410 may be of any suitable length or shape and may have any suitable characteristics or properties.

The proximal pressure sensor 412, the distal pressure sensor 414, and the distal flow sensor 416 may acquire data and send it to the processor of the system (e.g., the processor circuit 210 of FIG. 2). For example, the proximal pressure sensor 412 may be configured to continuously acquire pressure data at a location 490 along the vessel 400. The distal pressure sensor 414 may be configured to continuously acquire pressure data at a location 492 along the vessel 400. The distal flow sensor 416 may be configured to continuously acquire flow data at a location 494 along the vessel 400. In some embodiments, the flow sensor 416 may obtain flow data corresponding to a volume of blood which passes through the location 494 of the vessel 400 over time. In other embodiments, the flow sensor 416 may obtain flow velocity data relating to the velocity of blood moving through the vessel. For example, the flow velocity data obtained by the flow sensor 416 may include a speed and position of blood cells along a cross-section area of the vessel 400 or a three-dimensional region of the vessel. In some embodiments, any of the sensors (e.g., the pressure sensor 412, the pressure sensor 414, and/or the flow sensor 416) of the device 402 may be combined into one sensor or may be separate sensors. In one example, the distal pressure 414 and the flow sensor 416 may be a combined sensor configured to obtain both pressure data and flow data.

The processor circuit 210 may be configured to receive the pressure and flow data from the sensors of the device 402 to determine a fluid resistance measurement of the blood flow. A fluid resistance metric may correspond to the resistance of blood to flow through a particular length of the patient vasculature. The fluid resistance can be representative of the ability of a blood vessel (or a portion thereof) to flex/deform/dilate during blood flow. In the embodiment shown in FIG. 4, the device 402 may calculate a blood flow resistance value corresponding to the length 480 of the vessel. The length 480 may correspond to a distance measurement between the proximal pressure sensor 412 and the distal pressure sensor 414. In some embodiments, a relationship between the pressure and flow data may be established by the processor 206 to determine the fluid resistance of the blood flow along the length 480. In some embodiments, fluid resistance along the length 480 may be described by the equation, $F=\Delta P/Q$, where F is the fluid resistance, $\Delta P$ corresponds to a difference in pressure as measured by the distal pressure sensor 414 and the proximal pressure sensor 412, and Q corresponds to a flow measurement as measured by the flow sensor 416. It is understood that various constants or other variables may additionally affect the fluid resistance calculation as determined by the processor circuit 210 in response to various computer readable instructions stored on a memory in communication with the processor circuit.

The device 402 may be configured to measure fluid resistance as a metric to assess the sympathetic response to a stimulation of the sympathetic nervous system. Alternatively, the processor circuit 210 may analyze other physiological measurements obtained by the device 402 to assess sympathetic response. For example, the processor circuit 206 may be configured to analyze a pressure measurement of the proximal pressure sensor 412 and/or the distal pressure sensor 414 to assess sympathetic response. Flow measurements from the flow sensor 416 may also be used to assess sympathetic response.

Any of these changes in hemodynamic parameters may assist a physician in assessing conditions of a patient, as will be described in greater detail with reference to FIG. 8 and FIG. 9. For example, if a change in any of these parameters (e.g., pressure, flow, fluid resistance, etc.) is observed in response to stimulation of the sympathetic nervous system, the physician, or a processor circuit of the system (e.g., the circuit 210), may determine that the patient is a good candidate for a renal denervation procedure. In other cases, after a renal denervation procedure has been performed, an observed change in any of these parameters may indicate that the renal denervation procedure was successful. On the other hand, if these parameters do not change, the physician or a processor circuit may determine that the patient is not a good candidate for renal denervation or that a renal denervation procedure was not successfully performed. In some embodiments, the flow sensor 416 may be a thermoelectric sensor.

Figure 5:
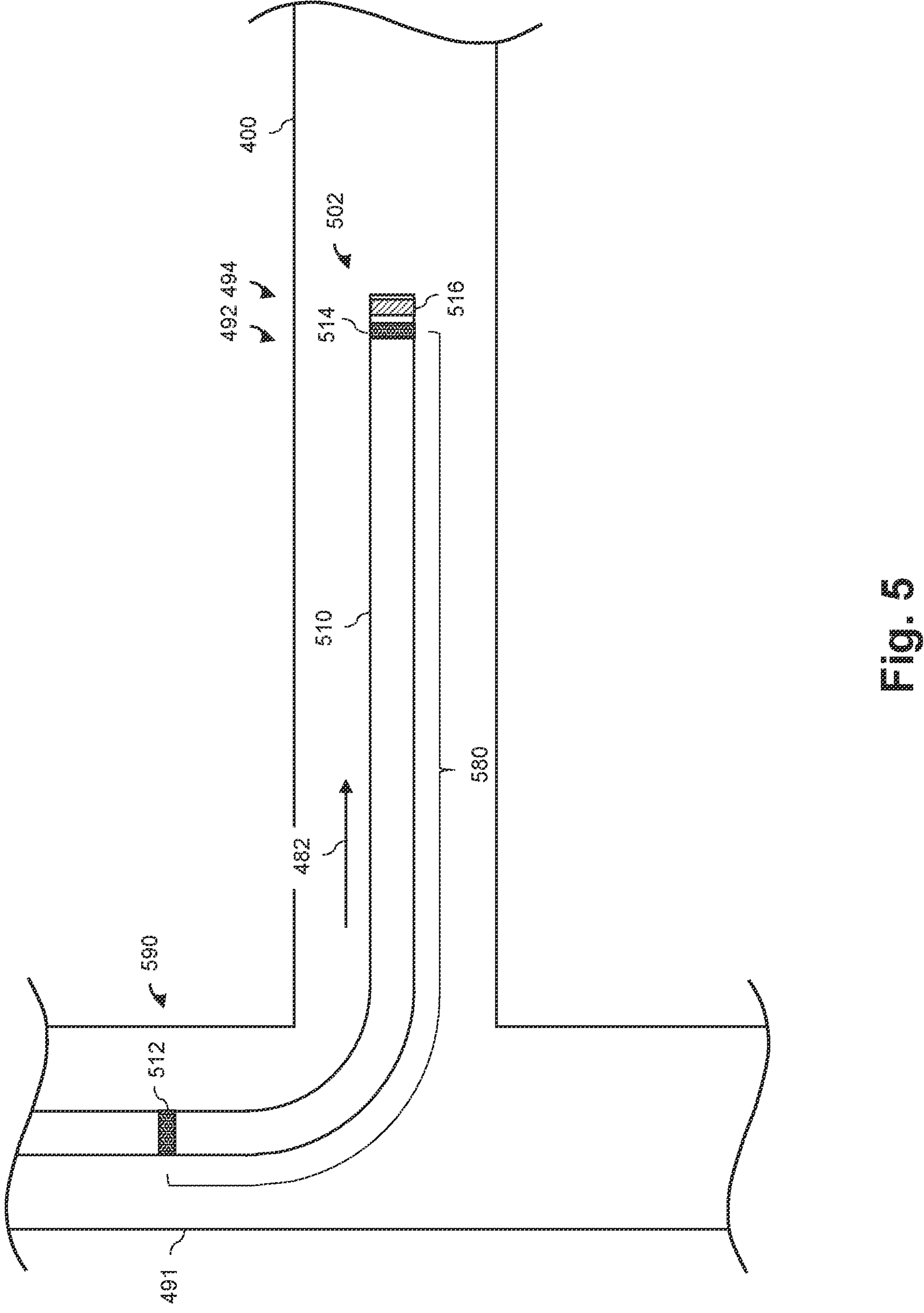
FIG. 5 is a diagrammatic view of an intravascular device positioned within the renal anatomy, according to aspects of the present disclosure.

FIG. 5 is a diagrammatic view of an intravascular device positioned within the renal anatomy, according to aspects of the present disclosure. The device 502 may be another embodiment of the device 102 described with reference to FIG. 1. The device 502 may be configured to receive various physiological measurements of the vessel 400. The device

502 may include a flexible elongate member 510, a proximal pressure sensor 512, a distal pressure sensor 514, and a blood flow sensor 516.

The device 502 may continuously receive distal pressure measurements by the distal pressure sensor 514 at the location 492. The proximal pressure sensor 512 may continuously receive proximal pressure measurements at the location 590. The flow sensor 516 may continuously receive flow measurements at the location 494. Any of the sensors of the device 502 may be substantially similar to any of the sensors of the device 402 described with reference to FIG. 4.

Like the device 402, the data obtained by the device 502 may be transmitted to a processor circuit of the system 100 (e.g., the processor circuit 210 of FIG. 2). The processor circuit 210 may be configured to calculate one or more fluid resistance measurements based on the data received by the device 502. In the embodiment shown in FIG. 5, the processor circuit 210 may determine a fluid resistance measurement corresponding to the length 580 between the proximal pressure sensor 512 and the distal pressure sensor 514.

It is noted that any suitable variation of a device configured to obtain pressure and flow measurements for a fluid resistance measurement may be included as part of the system 100 disclosed. For example, distal and proximal pressure sensors and/or blood flow sensors, such as any of those described herein, may be positioned at any suitable location along an intravascular device, such as the devices disclosed herein. Any sensors may be positioned on, for example, a guidewire, a catheter, a guide catheter, or any other suitable intravascular device.

In the embodiment shown in FIG. 5, the proximal pressure sensor 512 may be positioned within the aorta 491 of the patient while the distal pressure sensor 514 may be positioned within the renal artery 400. In this configuration, the device 502 may obtain measurements used to determine a flow resistance between the proximal pressure sensor 512 and the distal pressure sensor 514 as shown by the length 580. In some embodiments, with the proximal pressure sensor 512 positioned within the aorta 491 and the distal pressure sensor 514 positioned within the renal artery 400, differences in flow resistance measurements may be more pronounced and, therefore, more easily and reliably detected and compared. The extended spacing between the proximal pressure sensor 512 and the distal pressure sensor 514 may enable the proximal pressure sensor 512 to be positioned within a separate vessel (e.g., the aorta 491) from the distal pressure sensor 514 (e.g., positioned within the renal artery 400).

In some embodiments, the device 502 of FIG. 5 may advantageously provide a physician or user of the system 100 with an aortic pressure measurement in addition to a flow resistance measurement. In some embodiments, the aortic pressure measurement individually may provide the physician or user with an additional view into how the patient responds to stimulation of the sympathetic nervous system.

Figure 6:
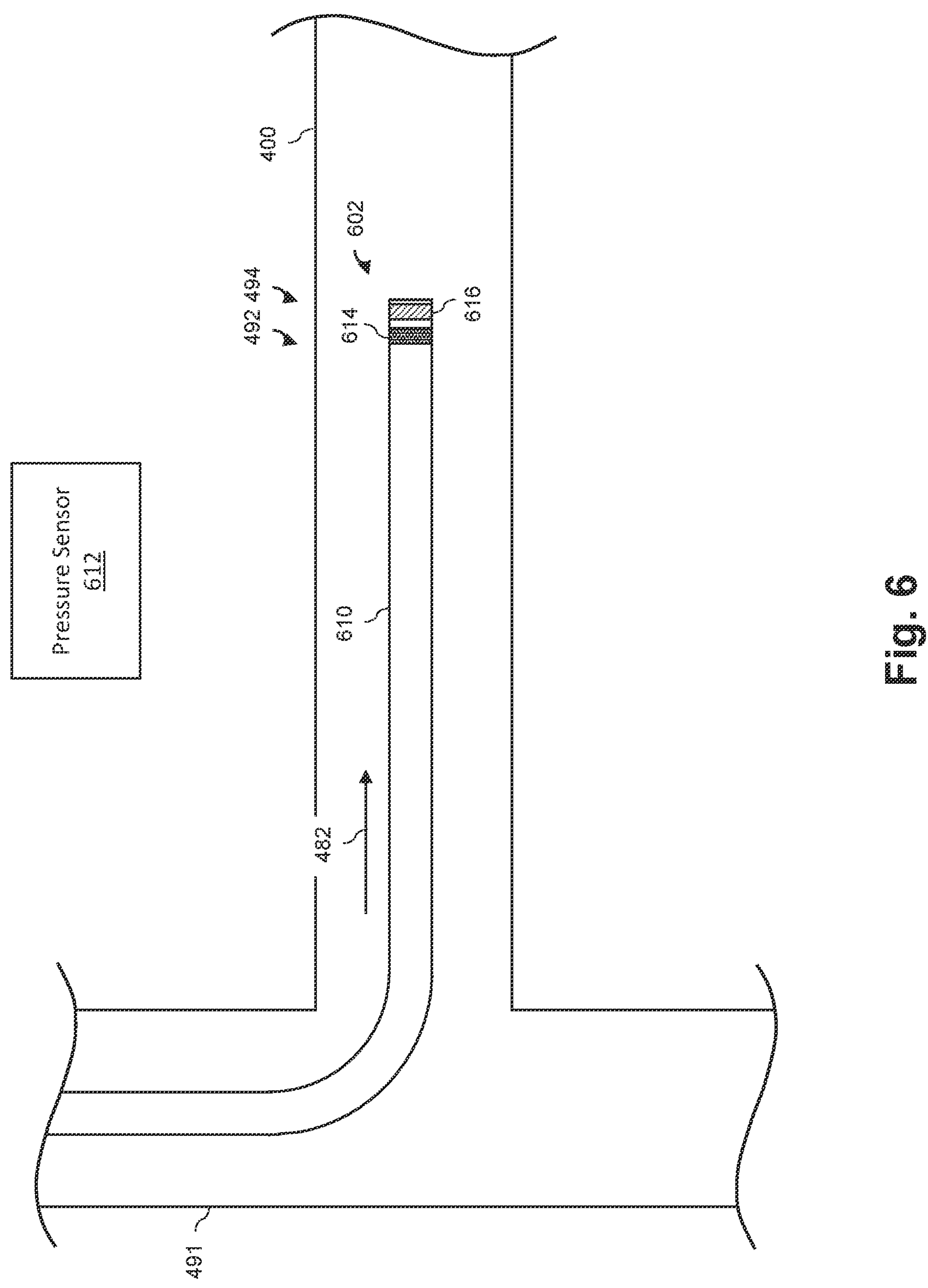
FIG. 6 is a diagrammatic view of an intravascular device positioned within the renal anatomy in conjunction with an additional pressure sensor, according to aspects of the present disclosure.

FIG. 6 is a diagrammatic view of an intravascular device 602 positioned within the renal anatomy, according to aspects of the present disclosure. The device 602 may be another embodiment of the device 102 described with reference to FIG. 1. The device 602 may be configured to receive various physiological measurements of the vessel 400. The device 602 may include a flexible elongate member 610, a distal pressure sensor 614, and a blood flow sensor 616. As shown in FIG. 6, an additional pressure sensor 612 may be used in conjunction with the intravascular device 602.

The device 602 may continuously receive distal pressure measurements by the distal pressure sensor 614 at the location 492. The flow sensor 616 may continuously receive flow measurements at the location 494. Any of the sensors of the device 602 may be substantially similar to any of the sensors of the device 402 described with reference to FIG. 4 and/or the device 502 described with reference to FIG. 5.

The pressure sensor 612 may be any suitable pressure sensor or device configured to measure the blood pressure of the patient. In some embodiments, the pressure sensor 612 may be a part of the same device 602 described previously. In some embodiments, the pressure sensor 612 may be a sensor of a different device (e.g., a distinct/different catheter or guidewire from the catheter or guidewire with the sensors 614, 616). In some examples, the pressure sensor 612 may be a part of, or may be an intravascular device (catheter or guidewire). In embodiments in which the pressure sensor 612 is part of an intravascular device, the sensor 612 may be positioned at any suitable location. For example, the sensor 612 may be positioned within the aorta 491. In such an example, the device with the sensor 612 may be positioned adjacent to or around the device 602. Similarly, the pressure sensor 612 may be positioned within the renal artery 400 on a device positioned adjacent to or around the device 602. In some aspects, the sensors 614, 616 can be positioned within the renal artery 400, while the sensor 612 is positioned in a different portion of the vasculature (not the renal artery 400), such as the abdominal aorta 491. Thus, the sensor 612 and/or the intravascular catheter/guidewire with the sensor 612 can be positioned outside of the vessel with the sensors 614, 616 (and/or the intravascular catheter or guidewire 602).

In some embodiments, the pressure sensor 612 may be positioned on an arterial line. In such an embodiment, the pressure sensor 612 may be positioned within a blood vessel in the finger, hand, wrist, or arm of a patient. In such an embodiment, the sensor 612 may alternatively be positioned at any other location within the patient vasculature. In some embodiments, the pressure sensor 612 may be an external device, such as a pressure measurement cuff, or any other external blood pressure measurement device. In some aspects, the second pressure measurement may be obtained by the pressure sensor 612 positioned outside the patient body, but which measures the pressure of fluid within a fluid filled column in communication with the blood within the patient vasculature, such as within the renal artery, aorta (e.g., abdominal aorta) or another blood vessel. The pressure sensor 612 can be coupled to the proximal portion (e.g., the proximal end) of the intravascular catheter (distinct/different from, e.g., the intravascular guidewire with the sensors 614, 616) such that the proximal end of the fluid filled column is in fluid communication with the pressure sensor 612. The fluid filled column can have an opening at a distal portion (e.g., distal end) of the intravascular catheter, with the opening positioned within the patient vasculature, such as within the renal artery, aorta (e.g., abdominal aorta), or another blood vessel. The pressure sensor 612 is in direct fluid communication with blood within the patient vasculature, such as within the renal artery, aorta (e.g., abdominal aorta) or another blood vessel. Thus, the measured blood pressure is representative of the blood pressure at a distal portion (e.g., distal end) of the intravascular catheter, but the pressure sensor itself may be located outside the patient body.

The device 602 and the device of the pressure sensor 612 may simultaneously be in communication with the control system 130 (FIG. 1). For example, in some embodiments, the communication interface 140 of the control system 130 may facilitate communication between the device 602 and the device of the pressure sensor 612. In this way, the control system 130, or a processor circuit of the control system 130 (e.g., the processor circuit 210 of FIG. 2) may direct the device 602 to obtain a pressure measurement with the pressure sensor 614 and to obtain a flow measurement with the flow sensor 616, and simultaneously direct the pressure sensor 612 to obtain a pressure measurement. These data may then be transmitted to the processor circuit 210. The processor circuit 210 may be configured to determine a fluid resistance measurement based on these received data. In some embodiments, particularly in embodiments in which the pressure sensor 612 includes an intravascular pressure sensor, this fluid resistance measurement may correspond to a distance between the sensor 614 of the device 602 and the pressure sensor 612. This fluid resistance measurement may be measured while the sympathetic nervous system is under stimulation and again when the sympathetic nervous system is not under stimulation. Fluid resistance measurements may then be compared to assess the patient's responsiveness to sympathetic nervous system stimulation.

Figure 7:
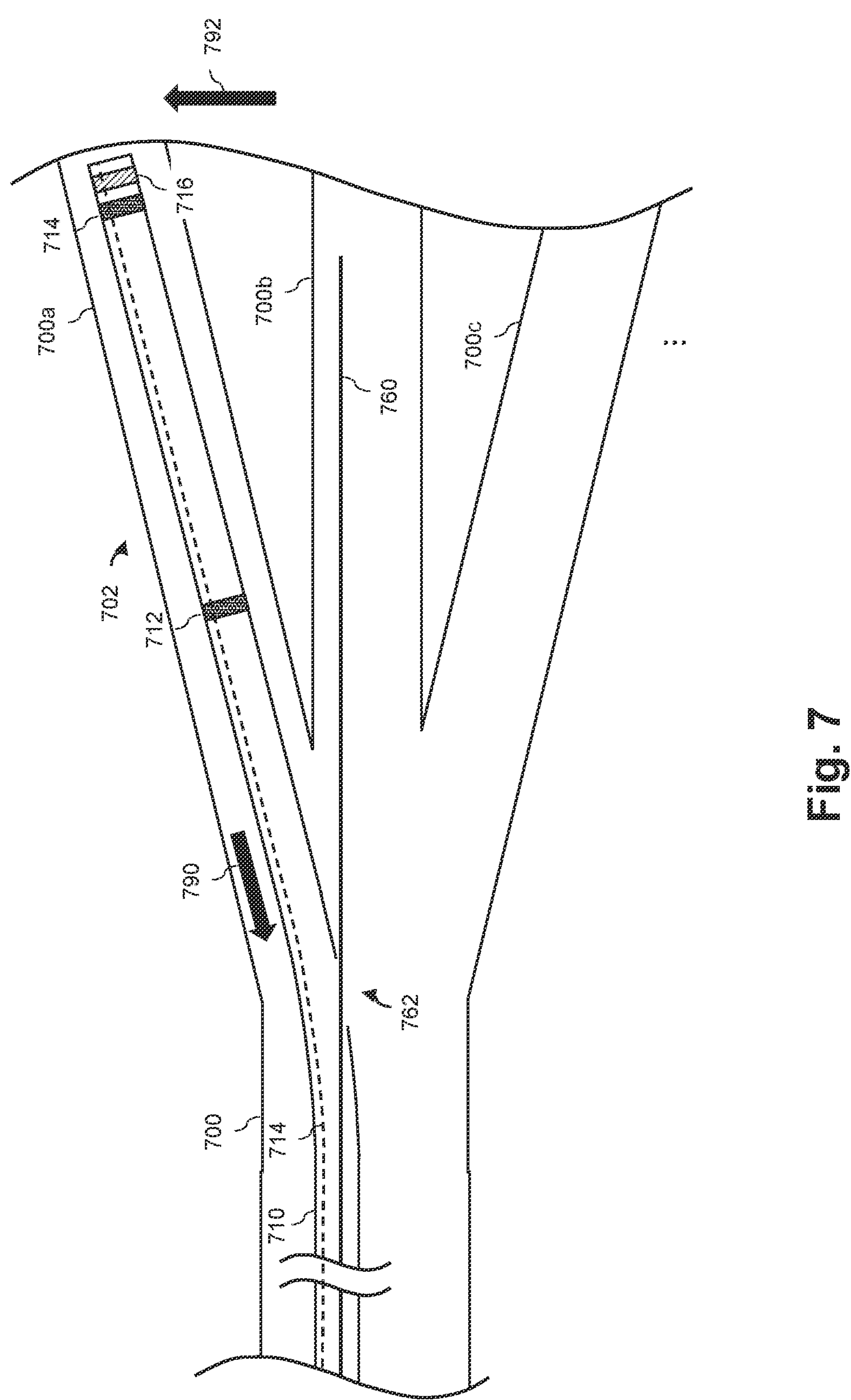
FIG. 7 is a diagrammatic view of an intravascular device positioned within a branch of the renal anatomy, according to aspects of the present disclosure.

FIG. 7 is a schematic diagram of an intravascular device 702, according to aspects of the present disclosure. The device 702 may be one embodiment of the device 102 described with reference to FIG. 1. As shown in FIG. 7, the device 702 may be configured to be positioned within a blood vessel of a patient. The device 702 shown in FIG. 7, like the devices previously described, may include structures configured to monitor the sympathetic response to stimulation of the sympathetic nervous system. The device 702 shown in FIG. 7 may include a deflectable member on the distal end of the catheter. This enables the user to preferentially select renal artery branches for measurement. This deflectable component may redirect the guidewire to the preferred arterial branch, or the deflectable component can redirect the catheter away from the guidewire which is already placed. This would enable measurement of multiple branches without the need to move the catheter or guidewire.

A renal artery 700 is shown in FIG. 7. The renal artery 700 may, at a distal end, split into multiple side branches. For example, a side branch 700*a*, a side branch 700*b*, and a side branch 700*c* are shown. It is noted that additional or fewer side branches may be included within the renal vasculature. The side branches 700*a*, 700*b*, and 700*c* may extend in a distal direction and terminate at a kidney (e.g., either of the kidneys 10 of FIG. 3).

In the embodiment shown, a portion of the device 702 may be positioned within one side branch (e.g., the side branch 700*a*) while a separate portion of the device 702 may be positioned within a different side branch (e.g., the side branch 700*b*). In some embodiments, the measurement portion of the device 702 (e.g., a proximal pressure sensor 712, a distal pressure sensor 714, and/or a distal flow sensor 716) may be moved to different side branches within the renal vasculature without completely removing the device 702.

As shown in FIG. 7, a guidewire 760 may extend along a longitudinal lumen of the device 702. In some embodiments, the guidewire 760 may be positioned within the renal artery first. In the embodiment shown, the guidewire 760 may be positioned within the side branch 700*b*. The device 702 may then be positioned around the guidewire 760. For example, a lumen of the device 702 may be sized to receive the guidewire 760. At the opening 762, the device 702 may be positioned around the guidewire 760. The device 702 may then be moved along the guidewire through the patient vasculature to the renal vasculature. There, the device 702 may be positioned within the same side branch 700*b* with the guidewire 760. After measurements are made there, however, the device 702 may be moved in a proximal direction so as to exit the side branch 700*b* and return to the primary renal artery 700. There, the measurement portion of the device 702 may be deflected from the guidewire 760 so as to be positioned in a separate side branch (e.g., the side branch 700*a*) while the guidewire 760 remains in the same side branch (e.g., the side branch 700*b*).

In some embodiments, the device may include one or more pull wires 770. A pull wire (e.g., the pull wire 770) may be positioned within the device 702 or on an outer surface of the device 702. In some embodiments, the pull wire 770 may be attached to a side of the device 702 or a side of the flexible elongate member 710 of the device 702. In this way, when a physician, or other automated or robotic system, pulls on the pull wire 770, a force is exerted in the proximal direction shown by the arrow 790. Due to the flexible nature of the device 702, this force on one side of the device 702 causes the device to deflect away from the guidewire 760 in a direction corresponding the to the location at which the pull wire 770 is attached to the device. This direction may be shown by the arrow 792.

The device 702 shown and described with reference to FIG. 7 may advantageously allow the physician or the user of the system 100 to obtain fluid resistance measurements within different branches of the renal vasculature for faster comparison. By assessing fluid resistance in multiple side branches of the renal vasculature, the physician or user may determine which branches of the renal vasculature may be most suited for a renal denervation procedure. For example, in some embodiments, a greater change in fluid resistance between a measurement made under stimulation verses a measurement made without stimulation may be measured within one side branch than another. This may assist a physician in determining that the side branch showing a greater change would be a better candidate for renal denervation.

Figure 8:
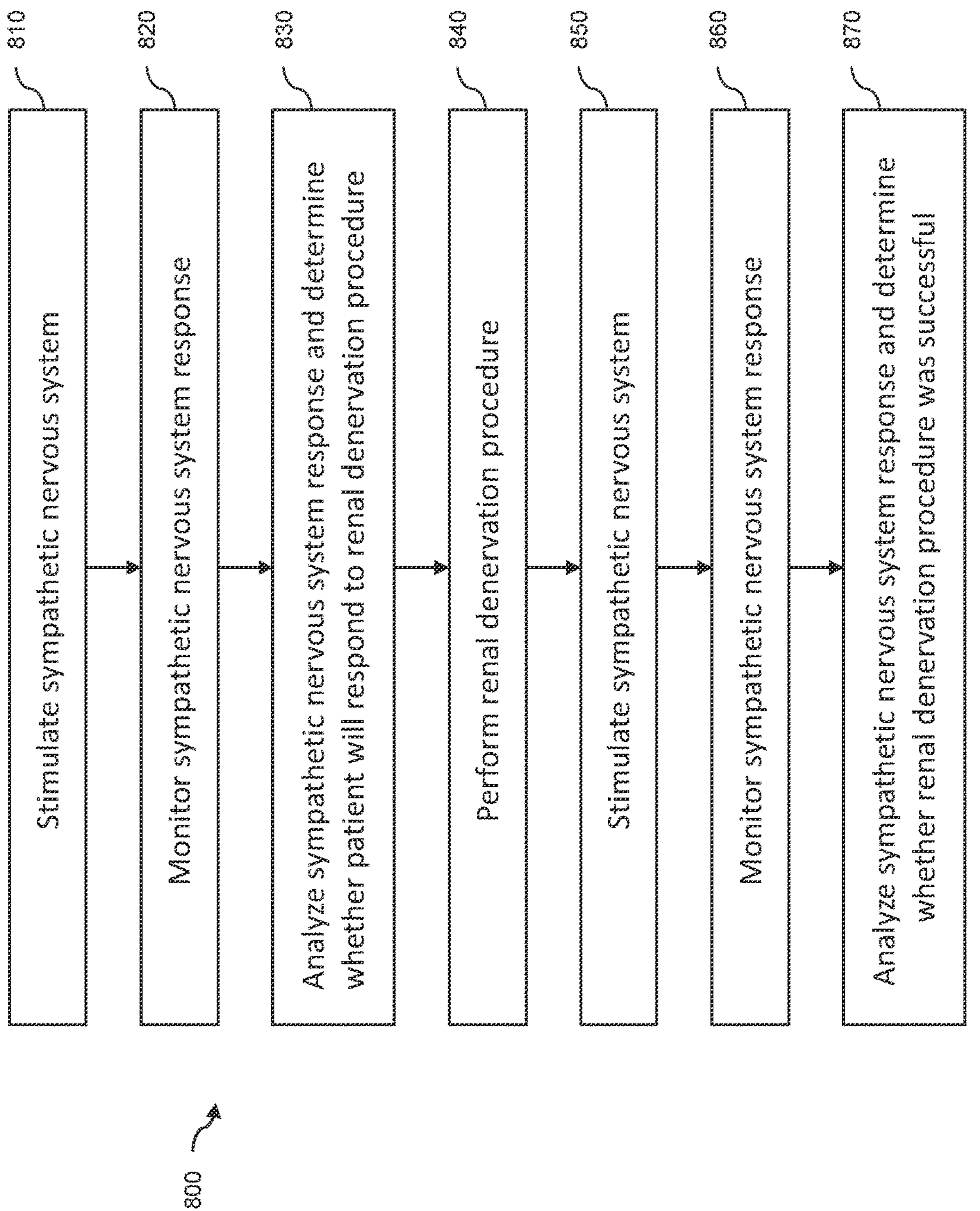
FIG. 8 is a flow diagram of a method of analyzing a sympathetic nervous system response, according to aspects of the present disclosure.
Figure 9:
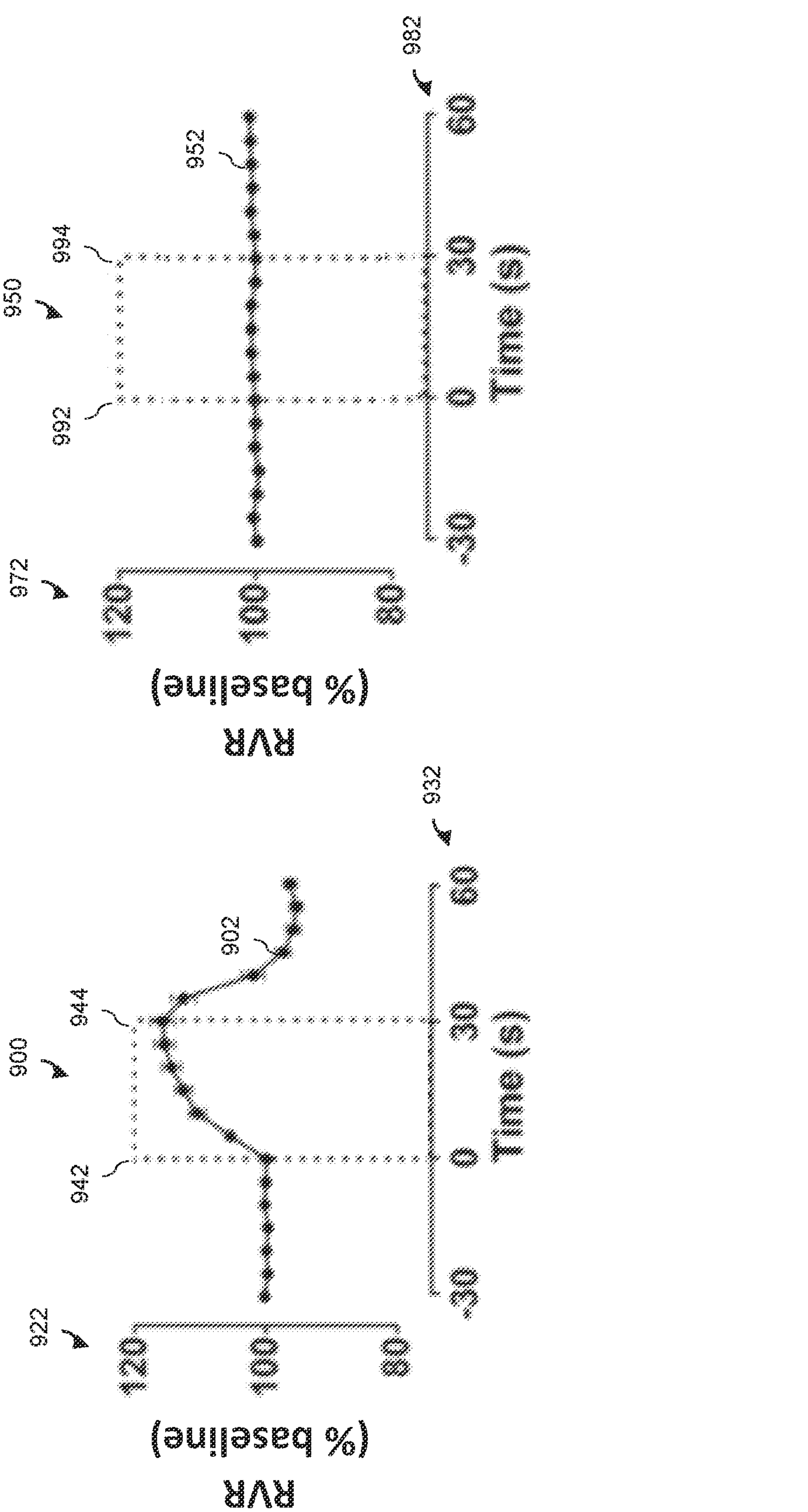
FIG. 9 is a diagrammatic view of plots of blood flow resistance, according to aspects of the present disclosure.

FIG. 8 is a flow diagram of a method of analyzing a sympathetic nervous system response, according to aspects of the present disclosure. The steps of the method 800 will be described with reference to FIG. 9. FIG. 9 is a diagrammatic view of plots of blood flow resistance, according to aspects of the present disclosure.

As illustrated, the method 800 includes a number of enumerated steps, but embodiments of the method 800 may include additional steps before, after, or in between the enumerated steps. In some embodiments, one or more of the enumerated steps may be omitted, performed in a different order, or performed concurrently. The steps of the method 800 can be carried out by any suitable component within the system 100 and all steps need not be carried out by the same component. In some embodiments, one or more steps of the method 800 can be performed by, or at the direction of, a processor circuit of the diagnostic system 100, including, e.g., the processor 260 (FIG. 2) or any other component.

At step 810, the method 800 includes stimulating the sympathetic nervous system. In some embodiments, the system 100 may include components configured to stimulate the sympathetic nervous system of the patient. For example, the system 100 may include various intravascular or extraluminal devices configured to stimulate the sympathetic nervous system. In some embodiments, another device or system, such as one separate from the system 100 may be used to stimulate the sympathetic nervous system of the patient. In some aspects, the nerves stimulated by various components of the system 100 may include nerves proximate to the renal blood vessel, or any other target vessel in which a nerve ablation procedure may be performed, or may be nerves that are a part of the nervous system but spaced from or remote from the renal blood vessel or other target vessel. In some aspects, the device used to ablate renal nerves (e.g., the endovascular device 1602) may be any suitable type of ablation device. For example, the ablation device may include an ultrasound-based ablation device or an alcohol-based ablation device.

In some examples, an intravascular device including a compliant balloon may be positioned within a renal artery of a patient. As the compliant balloon expands, the blood flow of the patient at the renal artery may be decreased. This in turn may cause renal nerves to respond to the reduction in blood flow by sending and receiving impulses from to or from the central nervous system. As a result, the renal artery may contract or expand. A compliant balloon configured to restrict blood flow may be positioned at any other location within the patient vasculature.

In some examples, an intravascular pump may move blood from one location of the vasculature to another location. A pump may, for example, be positioned within the renal artery. In this way, the blood flow within the renal artery may be altered thus stimulating the sympathetic nervous system and causing a response.

In some embodiments, an intravascular device may be positioned within the patient vasculature, for example, within the renal artery or within the carotid artery of a patient. The intravascular device may include one or more electrodes configured to emit electrical energy. As the electrodes emit electrical energy, the resulting electrical field may stimulate surrounding structures. For example, with such a device positioned within the renal artery, the renal nerves may be electrically stimulated. With the device positioned within the carotid artery, a carotid body may be electrically stimulated. The intravascular device may be positioned within any other location of the patient vasculature as well.

In some embodiments, a carotid body may be stimulated externally, for example by applying pressure to a region of the patient's neck corresponding to the carotid artery, by an external patch configured to emit electrical energy, or by any other method.

At step 820, the method 800 includes monitoring the sympathetic nervous system for a response to the stimulation. Step 820 may be performed by the devices described with reference to FIGS. 1, and 3-7 of the present disclosure. For example, the fluid resistance of the blood within a vessel of the patient may be determined during stimulation and compared with a measurement before or after stimulation.

At step 830, the method 800 includes analyzing the sympathetic nervous system response and determining whether the patient will respond to a renal denervation procedure. Referring to FIG. 9, FIG. 9 includes a plot 900 and a plot 950.

In one embodiment, the plot 900 may correspond to renal vascular resistance (RVR) measurements of one patient and the plot 950 may correspond to RVR measurements of another patient. For example, the plot 900 may correspond to a patient that is likely to respond well to renal denervation in decreasing hypertension, while the plot 950 may correspond to a patient which will not respond well to renal denervation in decreasing hypertension. In this way, the system 200 may help a physician stratify patients who are likely to be aided by a renal denervation procedure and patients who are likely not to be aided by a renal denervation procedure. In some embodiments, the plot 900 may correspond to RVR measurements of one location of a patient, for example, within one side branch of the renal vasculature, and the plot 950 may correspond to RVR measurements of a different location within the same patient, for example, within a different side branch of the renal vasculature.

The plot 900 may include an axis 922. The axis 922 may define a scale associated with renal vascular resistance measurements. The RVR axis 922 may provide a visual illustration of resistance within the renal artery. For example, it may provide a reference such that locations of resistance measurements may indicate the corresponding value. The range of the RVR axis 922 may be automatically adjusted by the processor circuit of the system 100 or may be adjusted by a user. The plot 950 includes a similar axis 972.

The plot 900 may additionally correspond to a time axis 932. The time axis 932 shown in FIG. 9 may illustrate elapsed time of a procedure. Any region of the time axis 932 may correspond to any time of the procedure. The time axis 932 may be continuously shifted so as to display the time of the most recent measurement and an arbitrary number of previous times as well. The plot 950 includes a similar axis 982.

The plot 900 may additionally include multiple RVR data points 902. Each RVR data point 902, or renal vascular resistance point, may include a two-coordinate data point including an RVR measurement value and a time value. The RVR measurement value may correspond to the fluid resistance measured by any of the devices described herein. The time value may correspond to the time along the time axis 932 at which the associated RVR measurement was acquired. In this way, the data points 902 may be positioned within the plot 900 so as to correspond to the resistance value and the time value. Similarly, the plot 950 may include multiple RVR data points 952.

The plot 900 includes a dotted line 942. The line 942 may be a vertical line corresponding to a time measurement. In one embodiment, the line 942 may correspond to the time at which the sympathetic nervous system started to be stimulated, by e.g., any of the methods previously described.

An additional dotted line 944 is also shown. The line 944 may be a vertical line corresponding to a time measurement and may be overlaid over all the plot 900. The line 944 may correspond to the time at which the sympathetic nervous system was no longer stimulated. The line 944 may be similar to the line 942 in that it may be of any suitable appearance. The plot 950 includes similar lines 992 and 994 denoting the start and stop of sympathetic nervous system stimulation.

It is additionally noted that all percentage or other values described herein are merely exemplary and for pedagogical purposes only. Any suitable values including percentages of baseline values of hemodynamic parameters may be contemplated.

In some embodiments, the processor circuit 210 of the system 100 may be configured to determine a likelihood that a renal denervation procedure will decrease hypertension within the patient. This likelihood may be based on a difference between the fluid resistance measurements obtained during stimulation of the sympathetic nervous system and the fluid resistance measurements obtained while the sympathetic nervous system is not stimulated. For example, a likelihood of success of a renal denervation procedure may be determined as a percentage, a ratio, a score, or in any other form. In some embodiments, a maximum fluid resistance measurement obtained during stimulation may be determined and a maximum fluid resistance measurement obtained without stimulation may be determined. A difference between these two maximums may be determined. The likelihood of success of a renal denervation procedure may be based on patient history of other patients. For example, for a given difference between a maximum fluid resistance under stimulation and a maximum baseline resistance, the processor circuit may receive a percentage or ratio corresponding to the number of patients of the same resistance difference who underwent a renal denervation procedure that resulted in a reduction in hypertension and the number of patients that underwent a renal denervation procedure that did not result in a reduction in hypertension. This percentage or ratio may correspond to or be the likelihood of success of a renal denervation procedure for a given patient. In some embodiments, the likelihood calculation may be based on additional data. For example, a deep learning network may be implemented to determine and/or quantify the likelihood of success of a renal denervation procedure based on past patient history, annotated data from experts in the field, or any other data.

In some aspects, any of the measurements or data described herein may be location specific. For example, in aspects in which an intravascular renal stimulation device is used to stimulate the nerves surrounding the renal artery (see e.g., step 810 of the method 800), the measurements of blood pressure or flow, flow resistance, and/or the likelihood of a successful renal denervation procedure, may be specific to the location of the intravascular renal stimulation device when the nerves are stimulated. In that regard, the device may be moved to various locations along the vessel and any or all of the steps of the method 800 may be repeated at different locations. As a result, the system 100 may compare the received measurements or calculations and use it to determine a location at which a renal denervation procedure would be most effective. In some aspects, this location may be displayed to a user via the display. The processor circuit may output this location information in any suitable way. For example, the location may be identified within an extraluminal imaging and determined via various co-registration methods. This location may be identified within the extraluminal image via an indicator overlaid over the image. This indicator may be placed automatically by the processor circuit and/or manually by a user of the system 100. In some aspects, the location may be identified via a binary value or binary indication. For example, a "yes" or "no" indication may be displayed adjacent to locations within an image. Other terms may include "good candidate", "bad candidate", "recommended", and "not recommended." In some aspects, if a future renal denervation procedure is likely, it may be provided as a value along a scale, or a term referring to a scale, such as "good", "medium", or "bad", or "low", "medium", or "high", referring to the degree of responsiveness of the sympathetic nervous system. In some aspects, the likelihood of success may be calculated and/or displayed as a value of a continuous numerical scale, such as a range of 1 to 10, 1 to 100, or any other suitable range.

In some aspects, the binary terms may be displayed in real time while the stimulation device is positioned within the vessel. In this way, the physician may identify locations within the vessel at which a renal denervation procedure is predicted to be successful.

In some aspects, metrics acquired by the system 100 may include a strain metric, mean arterial blood pressure, heart rate, blood flow, vascular impedance or conductance, or any other suitable metrics. For example, the system may acquire any of these metrics as a first metric while the sympathetic nervous system is not under stimulation. Then, the system may acquire a second metric of the same type as the first metric while the sympathetic nervous system is under stimulation. In that regard, step 830 of the method 800 may include comparing the first metric and the second metric. In that regard, the comparison may be a numerical value of a difference or a percentage difference.

In some aspects, step 830 of the method 800 may additionally include displaying any of the metrics previously described. For example, the system may output, to the display, the first metric obtained while the system is not under stimulation. The system may also or alternatively output, to the display, the second metric obtained while the system is under stimulation. In that regard, either of the first metric obtained while the sympathetic nervous system is not under stimulation or the second metric obtained while the sympathetic nervous system is under stimulation may be displayed as a graphical representation or a visual representation, including a numerical value, graph, chart, plot of values, or symbols. In some aspects, the graphical representation of the first metric and the graphical representation of the second metric may be simultaneously provided on a single screen display or on separate screen displays. In some aspects, the graphical representation of the first metric and the graphical representation of the second metric may be displayed individually at different times. In some examples, the graphical representation of the first metric and/or the graphical representation of the second metric may be displayed in response to a user input selecting the first metric or the second metric for display. In that regard, the graphical representation of the first metric and graphical representation of the second metric in response to the processor circuit receiving the first metric and/or the second metric and/or generating the graphical representations of either of the first metric and/or the second metric. In some aspects, the graphical representation of the first metric could be provided on the screen display first (i.e., only the graphical representation of the first metric without a display of the graphical representation of second metric) before the second metric is received or the graphical representation of the second metric is generated. After the second metric is received or the graphical representation of the second metric is generated, then the screen display may be updated or changed to additionally include the graphical representation of the second metric so that both are provided on the screen display simultaneously. In some aspects, the comparison of the first metric and the second metric may be output to the display as a visual or graphical representation on a graph, chart, plot of values, or any other suitable display. In some aspects, the comparison of the first metric and the second metric may highlight a difference between the first metric and the second metric.

At step 840, the method 800 includes performing a renal denervation procedure. A renal denervation procedure may include severing or otherwise disabling the nerves of the renal artery (e.g., the nerves 121 of FIG. 3). In this way, hypertension in a patient may be relieved. After a renal denervation procedure, the steps 850 through 870 may be performed to determine if the renal denervation procedure was successful, as described below. Renal denervation therapies involve the ablation of renal nerves surrounding the renal artery in order to cut off the sympathetic tone associated with hypertensive patients. This results in a reduction of blood pressure in patients that may be resistant to pharmaceutical therapies alone.

At step 850, the method 800 includes stimulating the sympathetic nervous system. The step 850 may be substantially similar to the step 810 previously described. The sympathetic nervous system may be stimulated in any of the ways described with reference to step 810.

At step 860, the method 800 includes monitoring the sympathetic nervous system for a response to the stimulation. The step 860 may be substantially similar to the step 820 previously described.

At step 870, the method 800 includes analyzing the sympathetic nervous system response and determining whether the renal denervation procedure was successful. The step 870 may be substantially similar to the step 830 previously described.

In some aspects, step 870 of the method 800 may additionally include displaying any of the metrics previously described. For example, the system may output, to the display, a metric obtained while the system is not under stimulation (e.g., an at-rest metric) after the renal denervation procedure was performed (see step 840). The system may also or alternatively output, to the display, an additional metric obtained while the system is under stimulation (e.g., an under-stimulation metric) and after the renal denervation procedure was performed. In that regard, either of the metric obtained while the sympathetic nervous system is not under stimulation or the metric obtained while the sympathetic nervous system is under stimulation may be displayed as a graphical representation or a visual representation, including a numerical value, graph, chart, plot of values, or symbols. In some aspects, the graphical representation of the at-rest metric and the graphical representation of the under-stimulation metric may be simultaneously provided on a single screen display or on separate screen displays. In some aspects, the graphical representation of the at-rest metric and the graphical representation of the under-stimulation metric may be displayed individually at different times. In some examples, the graphical representation of the at-rest metric and/or the graphical representation of the under-stimulation metric may be displayed in response to a user input selecting the at-rest metric or the under-stimulation metric for display. In that regard, the graphical representation of the at-rest metric and graphical representation of the under-stimulation metric in response to the processor circuit receiving the at-rest metric and/or the under-stimulation metric and/or generating the graphical representations of either of the at-rest metric and/or the under-stimulation metric. In some aspects, the graphical representation of the at-rest metric could be provided on the screen display first (i.e., only the graphical representation of the at-rest metric without a display of the graphical representation of under-stimulation metric) before the under-stimulation metric is received or the graphical representation of the under-stimulation metric is generated. After the under-stimulation metric is received or the graphical representation of the under-stimulation metric is generated, then the screen display may be updated or changed to additionally include the graphical representation of the under-stimulation metric so that both are provided on the screen display simultaneously. In some aspects, the comparison of the at-rest metric and the under-stimulation metric may be output to the display as a visual or graphical representation on a graph, chart, plot of values, or any other suitable display. In some aspects, the comparison of the at-rest metric and the under-stimulation metric may highlight a difference between the at-rest metric and the under-stimulation metric.

With reference again to FIG. 9, at the step 870, the plot 900 may correspond to renal vascular resistance (RVR) measurements of a renal artery before a renal denervation procedure is performed and the plot 950 may correspond to RVR measurements of the same renal artery after a renal denervation procedure is performed. In such an embodiment, the plot 900 and the plot 950 may be acquired by the same intravascular device (e.g., any of the devices described herein). As shown in FIG. 9, a user of the system 100 and/or a processor circuit may determine that a renal denervation procedure was successful based on a comparison of the data. As shown in the plot 900, an increase in fluid resistance was observed during the time period of sympathetic nervous system stimulation. However, in the plot 950, no significant change in fluid resistance was observed. This little to no change in resistance in response to sympathetic nervous system stimulation may indicate that the renal denervation procedure was successful, and that hypertension may be relieved with the ablation of the renal nerves. In some embodiments, the processor circuit may determine that a renal denervation procedure was successful based on determining a difference in a maximum, average, or minimum value of fluid resistance obtained during stimulation of the sympathetic nervous system and a maximum, average, or minimum value of a baseline fluid resistance. The processor circuit may determine that a renal denervation procedure was effective if this difference, as measured after the renal denervation procedure, is below a threshold difference in resistance. In some embodiments, a similar difference may be determined before a renal denervation procedure. The determination of a successful renal denervation procedure may include a comparison of the difference before the procedure with the difference after the procedure.

Either of the plots 900 and/or 950 may be displayed to a user by, for example, the display 132 of FIG. 1. In addition, any of the other sensor data described in the present disclosure may be displayed to a user by the display 132 in any suitable manner. For example, the data herein may be displayed as graphs, plots, numerical data, alpha-numeric text, visual representations including shapes, colors, patterns, or by any other means. In some embodiments, the processor circuit (e.g., the processor 134 and/or the processor circuit 210) may receive various user inputs relating to obtaining additional data, modifying data, modifying the display of data, or anything else.

Figure 10:
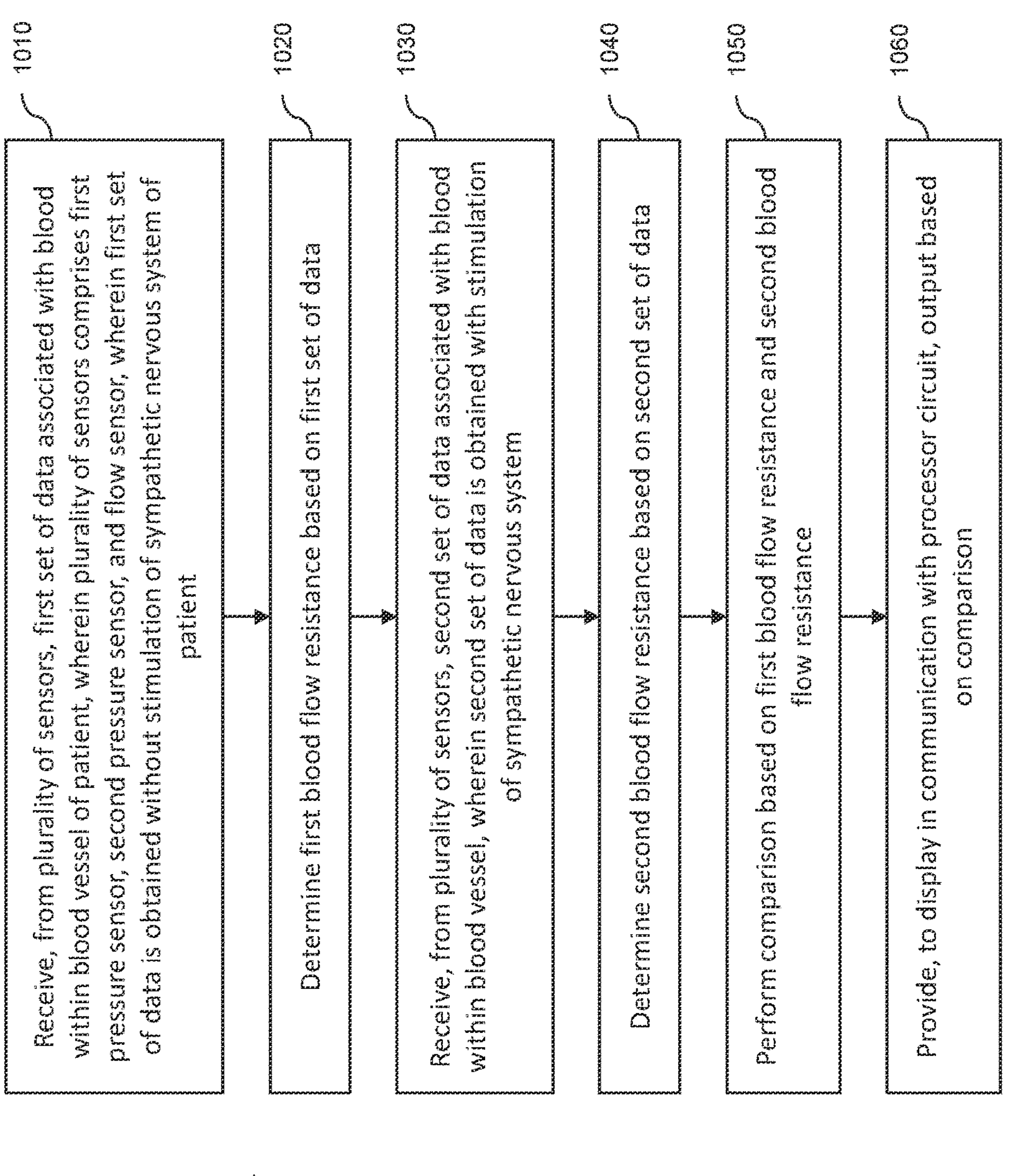
FIG. 10 is a flow diagram of a method of measuring blood flow resistance to assess a response of the sympathetic nervous system of stimulation, according to aspects of the present disclosure.

FIG. 10 is a flow diagram of measuring blood flow resistance to assess a response of the sympathetic nervous system of stimulation, according to aspects of the present disclosure. The method 1000 may describes an automatic segmentation of a vessel to detect segments of interest using co-registration of invasive physiology and x-ray images. As illustrated, the method 1000 includes a number of enumerated steps, but embodiments of the method 1000 may include additional steps before, after, or in between the enumerated steps. In some embodiments, one or more of the enumerated steps may be omitted, performed in a different order, or performed concurrently. The steps of the method 1000 can be carried out by any suitable component within the system 100 and all steps need not be carried out by the same component. In some embodiments, one or more steps of the method 1000 can be performed by, or at the direction of, a processor circuit of the diagnostic system 100, including, e.g., the processor 260 (FIG. 2) or any other component.

At step 1010, the method 1000 includes receiving, from a plurality of sensors, a first set of data associated with blood within a blood vessel of a patient, wherein the plurality of sensors comprises a first pressure sensor, a second pressure sensor, and a flow sensor, wherein the first set of data is obtained without stimulation of a sympathetic nervous system of the patient. In some aspects, step 1010 may include receiving a first set of data associated with blood within the renal artery and obtained without stimulation of a sympathetic nervous system of the patient.

At step 1020, the method 1000 includes determining a first blood flow resistance based on the first set of data. In some aspects, the blood flow resistance may be a blood flow resistance value or a blood flow resistance measurement. In some aspects, the first set of data may include a first pressure measurement, a second pressure measurement, and a flow measurement. These data may be used to calculate the blood flow resistance. In some aspects, the second pressure measurement may be obtained by a pressure sensor positioned within the blood vessel, such as the renal artery. In some aspects, the second pressure measurement may be obtained at another blood vessel (e.g., via an arterial line, or proximal or aortic pressure sensor coupled to a pressure sensing catheter with a fluid column). In some aspects, step 1020 includes determining a first renal vascular resistance based on the first set of data.

At step 1030, the method 1000 includes receiving, from the plurality of sensors, a second set of data associated with the blood within the blood vessel, wherein the second set of data is obtained with stimulation of the sympathetic nervous system. In some aspects, step 1030 includes receiving a second set of data associated with the blood within the renal artery, wherein the second set of data is obtained with stimulation of the sympathetic nervous system.

At step 1040, the method 1000 includes determining a second blood flow resistance based on the second set of data. In some aspects, step 1040 includes determining a second renal vascular resistance based on the second set of data.

At step 1050, the method 1000 includes performing a comparison based on the first blood flow resistance and the second blood flow resistance. In some aspects, step 1050 includes performing a comparison based on the first renal vascular resistance and the second renal vascular resistance.

At step 1060, the method 1000 includes providing, to a display in communication with the processor circuit, an output based on the comparison. In some aspects, step 1060 includes providing, to a display in communication with the processor circuit, an output based on the comparison, wherein the first set of data and the second set of data each respectively comprise: a first pressure measurement obtained by the first pressure sensor; a second pressure measurement obtained by the second pressure sensor; and a flow measurement obtained by the flow sensor. In some aspects, the output may alternatively be a metric obtained during stimulation and/or a metric obtained while the sympathetic nervous system of the patient is not under stimulation. In some aspects, the system 100 may determine and display the location of a recommended renal denervation procedure. This location may be displayed to a user on a screen display via an indication overlaid over an extraluminal image such as an x-ray image, a CT image, an MRI image, or any other suitable type of extraluminal image. In some aspects, the indication may be any suitable type of visual or graphical representation overlaid over a non-patient specific image, such as a cartoon or an illustration of an anatomy.

In some aspects, the screen display may include a metric obtained while the sympathetic nervous system was not under stimulation prior to the renal denervation procedure, a metric obtained while the sympathetic nervous system was under stimulation prior to the denervation procedure, a metric obtained while the sympathetic nervous system was not under stimulation after the renal denervation procedure, and a metric obtained while the sympathetic nervous system was under stimulation after the denervation procedure. Any of these metrics may be displayed on a single display simultaneously or at different times or on multiple displays simultaneously or at different times.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system comprising:

a processor circuit configured for communication with a first pressure sensor, a second pressure sensor, and a flow sensor, wherein the processor circuit is configured to:

determine if renal denervation is recommended for a patient based on a comparison between blood flow resistance with and without stimulation of a sympathetic nervous system of the patient, wherein the blood flow resistance is calculated using a single formula incorporating pressure and flow; and provide, to a display in communication with the processor circuit, an output based on if the renal denervation is recommended for the patient, wherein the blood flow resistance is distinct from fractional flow reserve (FFR), instant wave free ratio (iFR), and coronary flow reserve (CFR), wherein, to determine if the renal denervation is recommended for the patient, the processor circuit is configured to:

calculate a first value of the blood flow resistance using first pressure measurements and a first flow measurement obtained without the stimulation of the sympathetic nervous system; and calculate a second value of the blood flow resistance using second pressure measurements and a second flow measurement obtained with the stimulation of the sympathetic nervous system, wherein the output comprises a visual representation of the first value of the blood flow resistance and a visual representation of the second value of the blood flow resistance.

2. The system of claim 1, further comprising a first intravascular catheter or guidewire comprising the first pressure sensor and the flow sensor.

3. The system of claim 2, further comprising a second intravascular catheter or guidewire comprising the second pressure sensor.

4. The system of claim 1, further comprising an intravascular catheter or guidewire, wherein the intravascular catheter or guidewire comprises the first pressure sensor, the second pressure sensor, and the flow sensor.

5. The system of claim 1, wherein the first pressure measurements and the second pressure measurements each comprise:

a pressure measurement obtained by the first pressure sensor;

a pressure measurement obtained by the second pressure sensor; and wherein the first flow measurement and the second flow measurement are obtained by the flow sensor.

6. The system of claim 5, wherein the first pressure measurements and the first flow measurement are obtained simultaneously, wherein the second pressure measurements and the second flow measurement are obtained simultaneously.

7. The system of claim 1, wherein the comparison between the blood flow resistance with and without the stimulation of the sympathetic nervous system comprises a comparison between the first value of the blood flow resistance and the second value of the blood flow resistance.

8. The system of claim 7, wherein the comparison between the blood flow resistance with and without the stimulation of the sympathetic nervous system comprises a determination of whether a difference between the first value of the blood flow resistance and the second value of the blood flow resistance exceeds a threshold difference.

9. The system of claim 1, wherein the processor circuit is configured to: determine a location for the renal denervation based on the comparison between the blood flow resistance with and without the stimulation of the sympathetic nervous system, wherein the screen display comprises a visual representation based on the location.

10. The system of claim 1, wherein the single formula incorporating pressure and flow is $$F=\Delta P/Q,$$

where

F is the first value of the blood flow resistance, ΔP is a difference between the first pressure measurements, and Q is the first flow measurement, or F is the second value of the blood flow resistance, ΔP is a difference between the second pressure measurements, and Q is the second flow measurement.

11. The system of claim 1, wherein the processor circuit is configured to:

receive, from a plurality of sensors, a first set of data associated with blood within a blood vessel, wherein the first set of data is obtained without the stimulation of the sympathetic nervous system, wherein the plurality of sensors comprises the first pressure sensor, the second pressure sensor, and the flow sensor, wherein the first set of data comprises the first pressure measurements and the first flow measurement; and receive, from the plurality of sensors, a second set of data associated with the blood within the blood vessel, wherein the second set of data is obtained with the stimulation of the sympathetic nervous system, wherein the second set of data comprises the second pressure measurements and the second flow measurement.

12. The system of claim 11, wherein the blood vessel comprises a renal artery, and wherein the nerve comprises a renal nerve.

13. The system of claim 11, wherein the first set of data and the second set of data are obtained while:

the first pressure sensor and the flow sensor are positioned within the blood vessel; and the second pressure sensor is positioned outside of a body of the patient, wherein the second pressure sensor is in direct fluid communication with blood within the blood vessel.

14. The system of claim 11, wherein the first set of data and the second set of data are obtained while the first pressure sensor, the second pressure sensor, and the flow sensor are positioned within the blood vessel.

15. The system of claim 11, wherein the first set of data and the second set of data are obtained before the renal denervation, wherein, after the renal denervation, the processor circuit is further configured to:

determine a third value of the blood flow resistance based on a third set of data associated with the blood within the blood vessel and a fourth value of the blood flow resistance based on a fourth set of data associated with the blood within the blood vessel; and provide a further screen display to the display, wherein the further screen display comprises a visual representation of the third value of the blood flow resistance and the fourth value of the blood flow resistance.

16. The system of claim 15, wherein the processor circuit is configured to:

perform a comparison based on the third value of the blood flow resistance and the fourth value of the blood flow resistance;

determine if the renal denervation procedure was successful based on the comparison; and wherein the further screen display comprises a visual representation based on the determination of if the renal denervation was successful.

17. The system of claim 1, wherein the processor circuit is configured to:

generate a visual representation of the first value of the blood flow resistance; and generate a visual representation of the second value of the blood flow resistance.

* * * * *